US00PP23220P2

(12) United States Plant Patent
Kientzler

(10) Patent No.: US PP23,220 P2
(45) Date of Patent: Nov. 27, 2012

(54) **NEW GUINEA *IMPATIENS* PLANT NAMED 'VINFELECOR'**

(50) Latin Name: *Impatiens hawkeri*
Varietal Denomination: Vinfelecor

(75) Inventor: Ludwig Kientzler, Gensingen (DE)

(73) Assignee: VisioPlant, Alajuela (CR)

( * ) Notice: Subject to any disclaimer, the term of this patent is extended or adjusted under 35 U.S.C. 154(b) by 0 days.

(21) Appl. No.: 13/199,171

(22) Filed: Aug. 22, 2011

(51) Int. Cl.
*A01H 5/00* (2006.01)

(52) U.S. Cl. ..... Plt./318.1

(58) Field of Classification Search ..... Plt./318.1
See application file for complete search history.

*Primary Examiner* — Kent L Bell

(74) *Attorney, Agent, or Firm* — C. A. Whealy

(57) ABSTRACT

A new and distinct cultivar of New Guinea *Impatiens* plant named 'Vinfelecor', characterized by its compact, upright and mounded plant habit; freely branching habit; dense and bushy growth habit; dark green-colored leaves; and numerous large light red and pink-colored flowers that are positioned above and beyond the foliage.

1 Drawing Sheet

Botanical designation: *Impatiens hawkeri.*
Cultivar denomination: 'VINFELECOR'.

BACKGROUND OF THE INVENTION

The present invention relates to a new and distinct cultivar of New Guinea *Impatiens* plant, botanically known as *Impatiens hawkeri*, and hereinafter referred to by the name 'Vinfelecor'.

The new *Impatiens* plant is a product of a planned breeding program conducted by the Inventor in Gensingen, Germany. The objective of the breeding program was to develop new compact and freely branching *Impatiens* plants with numerous large flowers and attractive leaf and flower colors.

The new *Impatiens* plant originated from a cross-pollination made by the Inventor in October, 2006, of *Impatiens hawkeri* 'Tomini', not patented, as the female, or seed, parent with a proprietary selection of the *Impatiens hawkeri* identified as code number 06-035, not patented, as the male, or pollen, parent. The new *Impatiens* plant was discovered and selected by the Inventor as a flowering plant within the progeny of the stated cross-pollination in a controlled greenhouse environment in Gensingen, Germany in April, 2007.

Asexual reproduction of the new *Impatiens* plant by terminal cuttings propagated in a controlled greenhouse environment in Gensingen, Germany since the summer of 2010 has shown that the unique features of this new *Impatiens* plant are stable and reproduced true to type in successive generations of asexual reproduction.

SUMMARY OF THE INVENTION

Plants of the new *Impatiens* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Vinfelecor'. These characteristics in combination distinguish 'Vinfelecor' as a new and distinct New Guinea *Impatiens* plant:

1. Compact, upright and mounded plant habit.
2. Freely branching habit; dense and bushy growth habit.
3. Dark green-colored leaves.
4. Numerous large light red and pink-colored flowers that are positioned above and beyond the foliage.

Plants of the new *Impatiens* differ primarily from plants of the female parent, 'Tomini', in the following characteristics:

1. Plants of the new *Impatiens* are more compact and have shorter internodes than plants of 'Tomini'.
2. Plants of the new *Impatiens* are not as upright as plants of 'Tomini'.
3. Plants of the new *Impatiens* are more freely branching than plants of 'Tomini'.

Plants of the new *Impatiens* differ primarily from plants of the male parent selection in the following characteristics:

1. Plants of the new *Impatiens* have larger flowers than plants of the male parent selection.
2. Flower color of plants of the new *Impatiens* is more intense than flower color of plants of the male parent selection.

Plants of the new *Impatiens* can be compared to plants of New Guinea *Impatiens* 'Visinfdsg', disclosed in U.S. Plant Pat. No. 16,194. In side-by-side comparisons conducted in Gensingen, Germany, plants of the new *Impatiens* differed primarily from plants of 'Visinfdsg' in the following characteristics:

1. Plants of the new *Impatiens* were more compact than plants of 'Visinfdsg'.
2. Plants of the new *Impatiens* were more freely branching than plants of 'Visinfdsg'.
3. Plants of the new *Impatiens* had darker green-colored leaves than plants of 'Visinfdsg'.
4. Plants of the new *Impatiens* and 'Visinfdsg' differed in flower color as plants of 'Visinfdsg' had bright orange-colored flowers with whitish centers.

Plants of the new *Impatiens* can be compared to plants of New Guinea *Impatiens* 'Visinfdkp', disclosed in U.S. Plant Pat. No. 16,472. In side-by-side comparisons conducted in Gensingen, Germany, plants of the new *Impatiens* differed primarily from plants of 'Visinfdkp' in the following characteristics:

1. Plants of the new *Impatiens* were more freely branching than plants of 'Visinfdkp'.
2. Plants of the new *Impatiens* had larger flowers than plants of 'Visinfdkp'.
3. Plants of the new *Impatiens* and 'Visinfdkp' differed in flower color as plants of 'Visinfdkp' had dark pink-colored flowers.

BRIEF DESCRIPTION OF THE PHOTOGRAPHS

The accompanying photographs illustrate the overall appearance of the new *Impatiens* plant showing the colors as true as it is reasonably possible to obtain in colored reproductions of this type. Colors in the photographs may differ slightly from the color values cited in the detailed botanical description which accurately describe the colors of the new *Impatiens* plant.

The photograph at the bottom of the sheet comprises a side perspective view of a typical flowering plant of 'Vinfelecor' grown in a container.

The photograph at the top of the sheet is a close-up view of a typical flower of 'Vinfelecor'.

DETAILED BOTANICAL DESCRIPTION

The aforementioned photographs and following observations and measurements describe plants grown in Bonsall, Calif. during the winter and early spring in 10-cm containers in a polyethylene-covered greenhouse and under environmental conditions and cultural practices which approximate those generally used in commercial New Guinea *Impatiens* production. During the production of the plants, day temperatures averaged 27° C., night temperatures averaged 24° C. and light levels averaged 7,000 foot-candles. Measurements and numerical values represent averages for typical flowering plants which were 15 weeks old when the photographs and detailed description were taken. In the following description, color references are made to The Royal Horticultural Society Colour Chart, 2007 Edition, except where general terms of ordinary dictionary significance are used.

Botanical classification: *Impatiens hawkeri* 'Vinfelecor'.

Parentage:

*Female, or seed, parent.*—*Impatiens hawkeri* 'Tomini', not patented.

*Male, or pollen parent*.—Proprietary selection of *Impatiens hawkeri* identified as code number 06-035, not patented.

Propagation:

*Type*.—Vegetative cuttings.

*Time to initiate roots, summer*.—About 14 days at 20° C. to 22° C.

*Time to initiate roots, winter*.—About 18 days at 19° C. to 21° C.

*Time to produce a rooted young plant, summer*.—About 18 days at 20° C. to 22° C.

*Time to produce a rooted young plant, winter*.—About 21 days at 19° C. to 21° C.

*Root description*.—Fibrous, medium in thickness; white in color.

*Rooting habit*.—Moderately freely branching; medium density.

Plant description:

*Plant form*.—Compact, upright and mounded plant habit.

*Growth and branching habit*.—Vigorous and freely branching habit; about six lateral branches developing at the base; dense and bushy growth habit; pinching, that is, removal of the terminal apices, is typically not required, but will enhance branching.

*Plant height*.—About 18.5 cm.

*Plant diameter or spread*.—About 17 cm.

*Lateral branches*.—Length: About 4.6 cm. Diameter: About 5 mm. Internode length: About 2.1 cm. Texture: Smooth, glabrous. Color: Close to 187A.

Foliage description:

*Arrangement*.—Opposite or in whorls, simple.

*Length*.—About 10.6 cm.

*Width*.—About 3.3 cm.

*Shape*.—Elliptical.

*Apex*.—Acuminate.

*Base*.—Attenuate.

*Margin*.—Serrulate with ciliation.

*Texture, upper and lower surfaces*.—Smooth, glabrous.

*Venation pattern*.—Pinnate.

*Color*.—Developing leaves, upper surface: Close to N137A. Developing leaves, lower surface: Close to 137C. Fully expanded leaves, upper surface: Darker than 147A; venation, close to 147B. Fully expanded leaves, lower surface: Close to 147B; venation, close to 183D.

*Petiole*.—Length: About 1.8 cm. Diameter: About 3 mm. Texture, upper and lower surfaces: Smooth, glabrous. Color, upper and lower surfaces: Close to 177C.

Flower description:

*Flower type and flowering habit*.—Single axillary flowers; freely flowering habit with usually about eight flowers and flower buds per lateral branch; flowers positioned above the foliar plane and typically face upright and outwardly.

*Flower longevity*.—Flowers last about one week under greenhouse conditions; petals self-cleaning, gynoecium persistent.

*Fragrance*.—None detected.

*Natural flowering season*.—Year-round under greenhouse conditions; in the garden, flowering from spring until fall in California; plants begin flowering about ten weeks after planting.

*Flower size*.—Diameter: About 5.8 cm. Depth: About 3 cm.

*Flower buds*.—Length: About 2.1 cm. Diameter: About 1.4 cm. Shape: Ovoid. Color: Close to 54A.

*Petals*.—Quantity and arrangement: Five petals arranged in a single whorl. Length, banner petal: About 2.2 cm. Length, lateral petals: About 3 cm. Length, lower petals: About 3.5 cm. Width, banner petal: About 4.2 cm. Width, lateral petals: About 3.6 cm. Width, lower petals: About 4.1 cm. Shape: Cordate. Apex: Emarginate to cordate. Base: Acute. Margin: Entire. Texture, upper and lower surfaces: Smooth, glabrous; velvety. Color: When opening, upper surface: Center, close to N57C; towards the apex, close to 52A. When opening, lower surface: Close to N57C to N57D. Fully opened, upper surface: Towards the margins, close to 51A; at the apex, close to 43A; towards the base, close to 63C; at base, close to N57C; color does not fade with development. Fully opened, lower surface: Towards the apex, close to 55B; towards the base, close to 43A to 43B.

*Sepals*.—Quantity and arrangement: Three arranged in a single whorl; one modified into an elongated spur.

Length: About 7 mm. Width: About 5 mm. Shape: Elliptical. Apex: Acuminate. Base: Obtuse. Margin: Entire. Texture, upper and lower surfaces: Smooth, glabrous. Color, upper and lower surfaces: Close to 187D. Spur length: About 5.3 cm. Spur diameter: At flower, about 2 mm; at apex, less than 1 mm. Spur texture: Smooth, glabrous. Spur color: Close to 187D.

*Peduncles*.—Length: About 4 cm. Diameter: About 2 mm. Angle: About 35° to 45° from vertical. Strength: Strong. Texture: Smooth, glabrous. Color: Close to 182B.

*Reproductive organs*.—Stamens: Quantity: Five fused at anthers; filaments free. Anther size: About 4 mm by 6 mm. Anther color: Close to 159A. Pollen amount: Moderate. Pollen color: Close to 158A. Pistils: Quantity per flower: One. Pistil length: About 4 mm. Stigma shape: Rounded. Stigma color: Close to 145D. Style color: Close to 145B. Ovary color: Close to 145B.

*Seeds and fruit*.—Seed and fruit development have not been observed on plants of the new *Impatiens*.

Disease/pest resistance: Plants of the new *Impatiens* have not been observed to be resistant to pathogens and pests common to New Guinea *Impatiens*.

Temperature tolerance: Plants of the new *Impatiens* have been observed to tolerate temperatures from about 16° C. to about 35° C.

It is claimed:

1. A new and distinct New Guinea *Impatiens* plant named 'Vinfelecor' as illustrated and described.

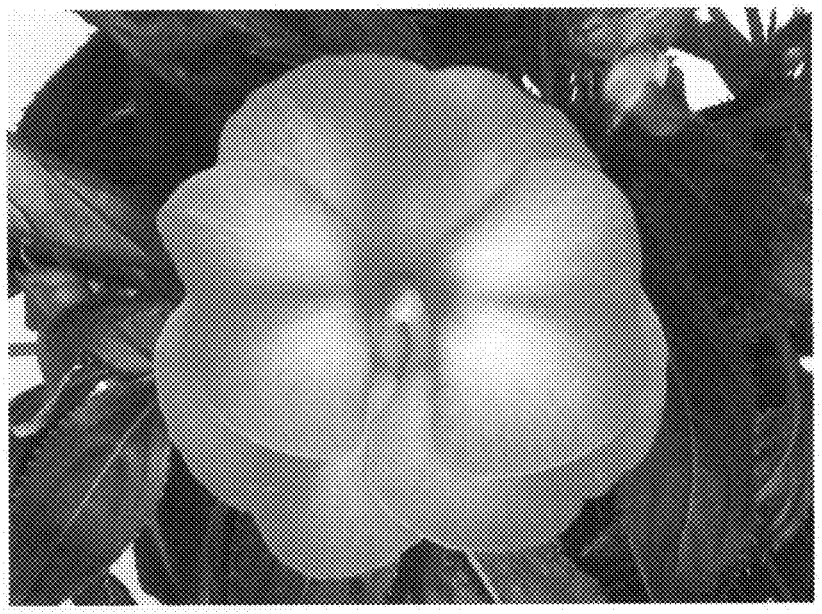
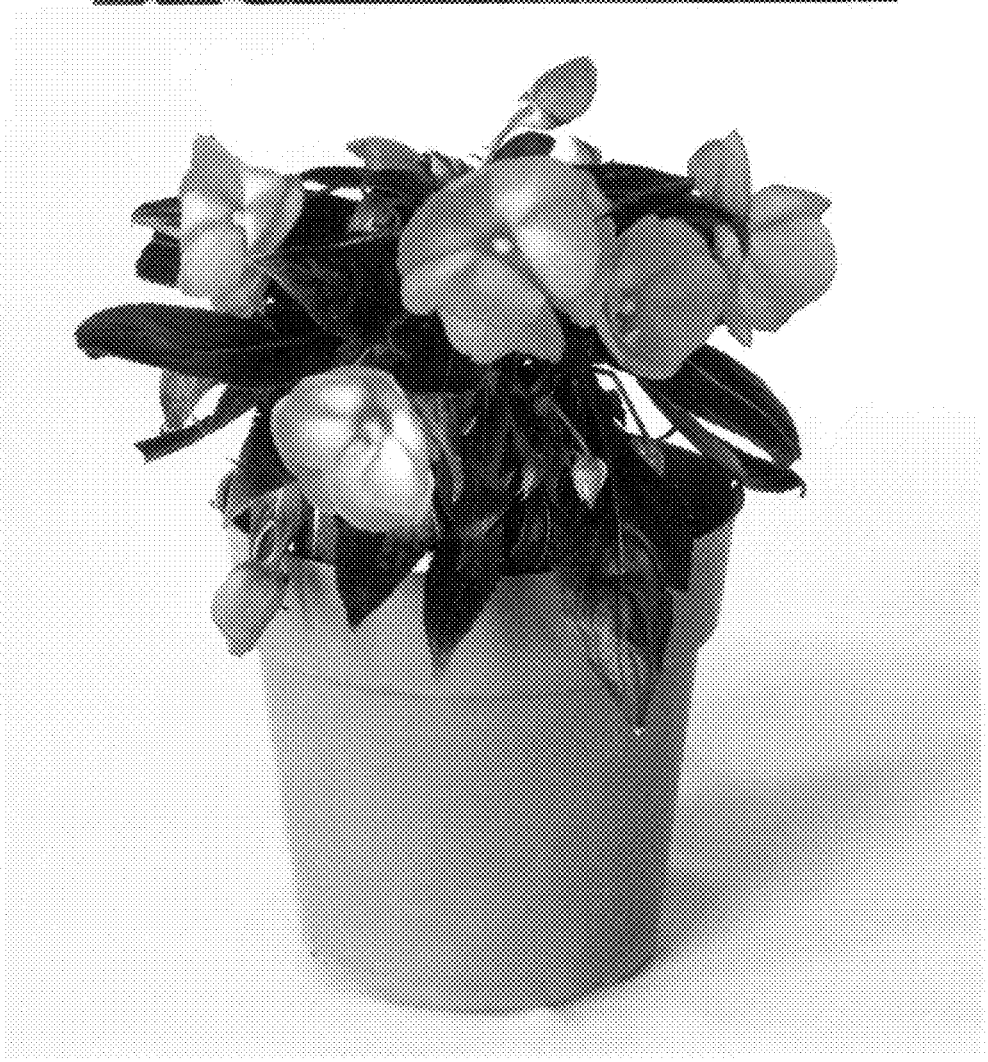

* * * * *